United States Patent
Wei et al.

(10) Patent No.: US 11,958,863 B2
(45) Date of Patent: Apr. 16, 2024

(54) BINDING COMPETITORS FOR USE IN MACROPHILIN-BINDING PHARMACEUTICAL ASSAYS AND METHODS OF USE THEREOF

(71) Applicant: Siemens Healthcare Diagnostics Inc., Tarrytown, NY (US)

(72) Inventors: Tie Wei, Wilmington, DE (US); Zhu Teng, Garnet Valley, PA (US); Martin Drinan, Newark, DE (US); Jie Li, Middletown, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 505 days.

(21) Appl. No.: 17/250,907

(22) PCT Filed: Oct. 25, 2019

(86) PCT No.: PCT/US2019/058058
§ 371 (c)(1),
(2) Date: Mar. 25, 2021

(87) PCT Pub. No.: WO2020/092153
PCT Pub. Date: May 7, 2020

(65) Prior Publication Data
US 2022/0024946 A1 Jan. 27, 2022

Related U.S. Application Data

(60) Provisional application No. 62/754,913, filed on Nov. 2, 2018.

(51) Int. Cl.
*C07D 498/18* (2006.01)
*G01N 33/94* (2006.01)

(52) U.S. Cl.
CPC ....... *C07D 498/18* (2013.01); *G01N 33/9493* (2013.01)

(58) Field of Classification Search
CPC ............................ C07D 498/18; A61K 31/436
USPC ......................................... 540/456; 514/291
See application file for complete search history.

(56) References Cited

U.S. PATENT DOCUMENTS

| 5,532,137 A | 7/1996 | Niwa et al. |
| 6,187,547 B1 | 2/2001 | Legay et al. |
| 6,635,745 B2 | 10/2003 | Sedrani et al. |
| 7,186,518 B2 | 3/2007 | Wang et al. |
| 7,223,553 B2 | 5/2007 | Roberts et al. |
| 8,039,599 B1 | 10/2011 | Sedrani et al. |
| 8,039,600 B2 | 10/2011 | Sedrani et al. |
| 8,586,322 B2 | 11/2013 | Wei |
| 2004/0092436 A1 | 5/2004 | Sakai et al. |
| 2005/0112778 A1 | 5/2005 | Wang et al. |
| 2006/0246518 A1 | 11/2006 | Chen et al. |
| 2009/0155929 A1 | 6/2009 | Wie et al. |
| 2009/0176213 A1 | 7/2009 | Zheng et al. |
| 2009/0317411 A1 | 12/2009 | Wong et al. |
| 2013/0236918 A1 | 9/2013 | Wei |
| 2014/0154706 A1 | 6/2014 | Zheng et al. |

FOREIGN PATENT DOCUMENTS

| CN | 102617729 | 8/2012 |
| JP | H09-5022272 | 3/1997 |
| JP | 2002509555 | 3/2002 |
| JP | 2007512340 | 5/2007 |
| JP | 2011506973 | 3/2011 |
| JP | 2016501374 | 1/2016 |
| KR | 10-2013-0015838 | 2/2013 |
| WO | 9507468 | 3/1995 |
| WO | 2012026665 | 3/2012 |
| WO | 2013022238 | 2/2013 |
| WO | 2015106283 | 7/2015 |

OTHER PUBLICATIONS

Wei Tie Q et al: "Sandwich assay for tacrolimus using 2 antitacrolimus antibodies"; Clinical Chemistry APR (2014), vol. 60, No. 4, pp. 621-630.
International Search Report for PCT/US2019/058058 dated Jan. 2, 2020.
Atomic structure of the rapamycin human immunophilin FKBP-12 complex, Gregory D. Van Duyne, Robert F. Standaert, Stuart L. Schreiber, and Jon Clardy J. Am. Chem. Soc., v.113 (19), pp. 7433-7434, (1991).
Atomic structure of the human immunophilin FKBP-12 complexes with FK506 and rapamycin Gregory D. Van Duyne et al., J. Mol. Biol. (1993) v. 229, pp. 105-124.
Nashan, B., The role of certican (everolimus, rad) in the many pathways of chronic rejection, Transplantation Proceedings (2001) 33: 3215-3230.

*Primary Examiner* — Jeffrey H Murray

(57) ABSTRACT

The present disclosure includes compounds, kits, and assay procedures for use in determining the levels of certain types of drugs in samples that contain specific binding proteins for the drugs. The present disclosure includes analog compounds useful for displacing the drugs from their endogenous binding proteins, and kits including same, as well as methods that utilize these displacers as binding competitors in pharmaceutical assays.

20 Claims, 1 Drawing Sheet

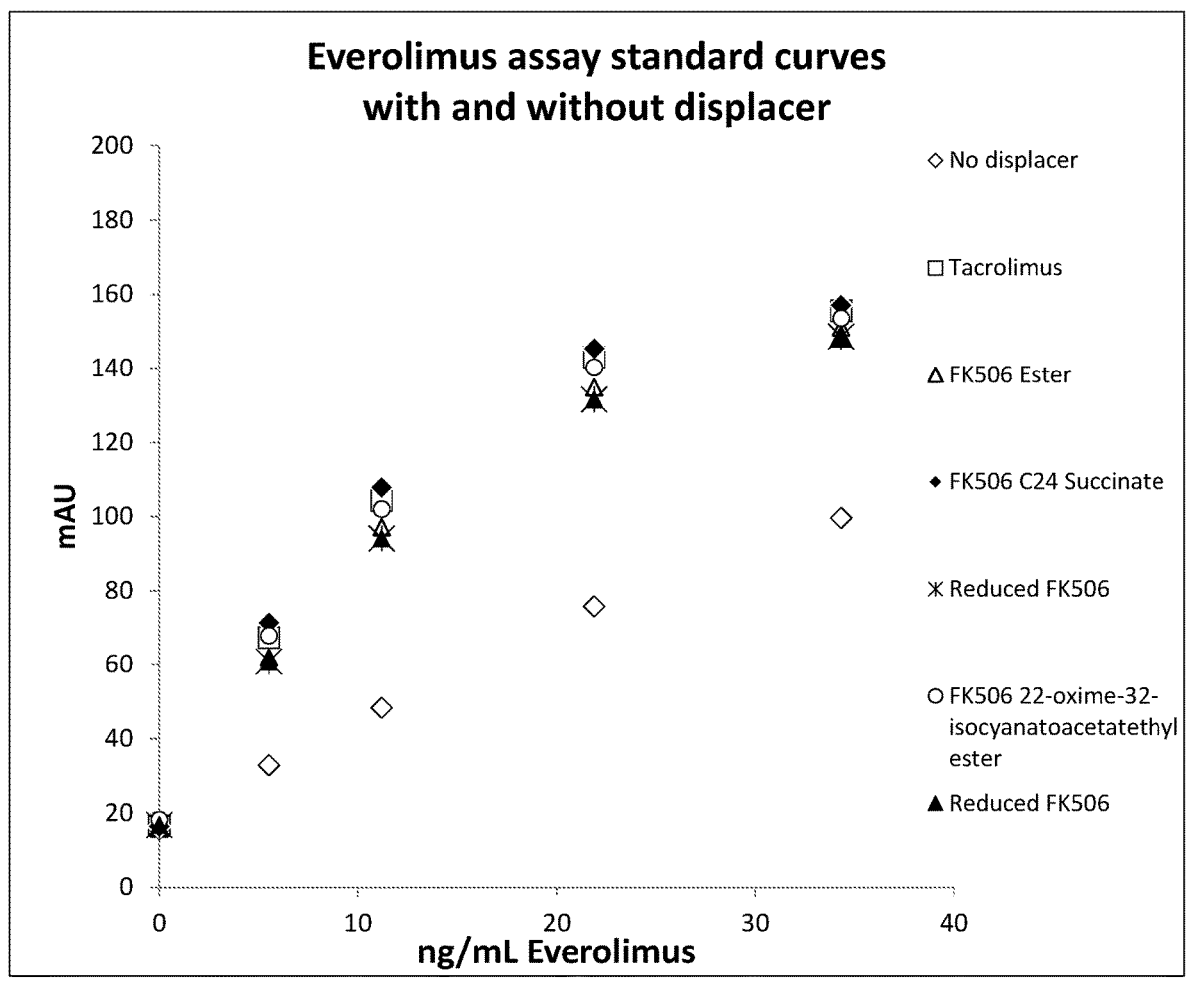

BINDING COMPETITORS FOR USE IN MACROPHILIN-BINDING PHARMACEUTICAL ASSAYS AND METHODS OF USE THEREOF

CROSS REFERENCE TO RELATED APPLICATIONS/INCORPORATION BY REFERENCE STATEMENT

The subject application claims benefit under 35 USC § 119(e) of U.S. provisional Application No. 62/754,913, filed Nov. 2, 2018. The entire contents of the above-referenced patent application are hereby expressly incorporated herein by reference.

STATEMENT REGARDING FEDERALLY SPONSORED RESEARCH OR DEVELOPMENT

Not Applicable.

TECHNICAL FIELD

The present disclosure is related to compounds, kits, and assay procedures for use in determining the levels of certain types of drugs in samples that contain specific binding proteins for the drugs. The present disclosure is related to analog compounds that are useful for displacing the drugs from their endogenous binding proteins, and kits comprising same, as well as methods that utilize these displacers as binding competitors in pharmaceutical assays.

BACKGROUND

The body relies upon a complex immune response system to distinguish self from non-self. At times, the body's immune system must be controlled in order to either augment a deficient response or suppress an excessive response. For example, when organs such as kidney, heart, heart-lung, bone marrow, and liver are transplanted in humans, the body will often reject the transplanted tissue by a process referred to as allograft rejection.

In treating allograft rejection, the immune system is frequently suppressed in a controlled manner with drug therapy. Immunosuppressant drugs are therapeutic drugs that are carefully administered to transplant recipients in order to help prevent allograft rejection of non-self tissue. Immunosuppressive drugs include (but are not limited to): glucocorticoids, cytostatics, antibodies, drugs acting on immunophilins, and other drugs such as (but not limited to) interferons, opiates INF binding proteins, mycophenolate, FTY720, and the like. A particular class of immunosuppressant drugs comprises those drugs that act on immunophilins. Immunophilins are an example of high-affinity, specific binding proteins having physiological significance. Two distinct families of immunophilins are presently known: cyclophilins and macrophilins (FK binding proteins or FKBPs, such as, but not limited to, FKBP12), the latter of which specifically bind, for example (but not by way of limitation), tacrolimus, sirolimus, or everolimus.

Two most commonly administered immunosuppressive drugs to prevent organ rejection in transplant patients are cyclosporine (CSA) and tacrolimus (FK506). Another drug that finds use as an immunosuppressant in the United States and other countries is sirolimus, also known as rapamycin. Derivatives of sirolimus are also useful as immunosuppressants; such derivatives include, for example (but not by way of limitation), everolimus and the like.

Tacrolimus, also known as FK506, is a cyclic, poly-N-methylated undecapeptide that possesses immunosuppressive activity and that is isolated from the fermentation product of the bacteria *Streptomyces tsukubaensis* No 9993. The structure of FK506 is shown in Formula I below.

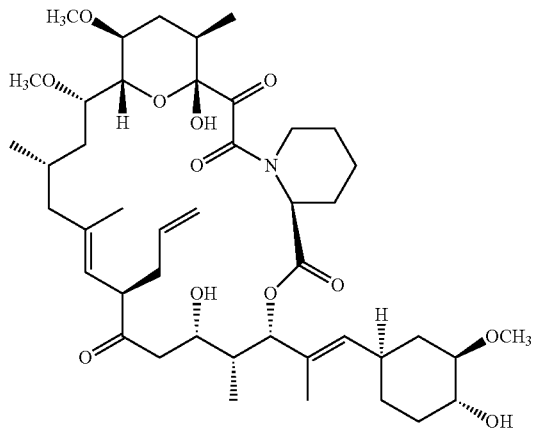

Formula I

Tacrolimus is commonly used, often along with other immunosuppressant drugs, to reduce graft rejection in allogeneic organ transplants by suppressing the immune system. Tacrolimus has a narrow therapeutic window, and thus it is critical to monitor blood drug concentrations for optimal efficacy. For tacrolimus drug monitoring, competitive immunoassays employing a single antibody are commercially available, and a sandwich immunoassay, which should offer higher analytical sensitivity and specificity and wider dynamic ranges than the competitive format, has been described (Wei et al., *Clinical Chemistry* (2014) 60(4):621-630; and U.S. Pat. No. 8,586,322).

Sirolimus, also known as rapamycin, is a macrolide antibiotic produced by *Streptomyces hygroscopicus*, and has been found to be pharmaceutically useful in a variety of applications, particularly as an immunosuppressant, e.g., for use in the treatment and prevention of organ transplant rejection and autoimmune diseases. The structure of sirolimus (rapamycin) is shown in Formula II below.

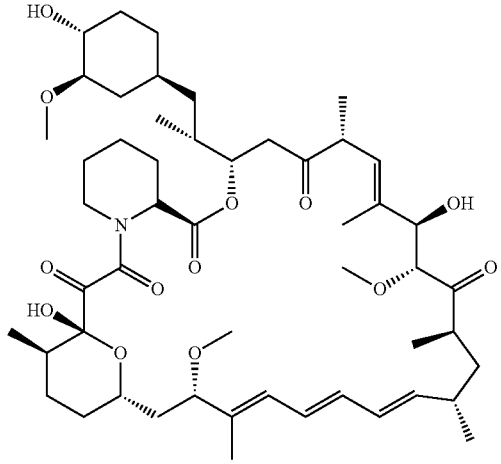

Formula II

Sirolimus, however, does exhibit side effects at higher dosages, and it has a somewhat variable bioavailability. Monitoring blood levels of rapamycin in patients being treated with rapamycin is thus very desirable in order to be able to regulate the dosage so as to maintain the minimum level sufficient for pharmacologic activity and to avoid any undue risk of side effects. Rapamycin assays have recently been described in U.S. Pat. Nos. 6,635,745; 8,039,599; and 8,039,600.

Everolimus [40-O-(2-hydroxyethyl)-rapamycin], also known as SDZ-RAD, RAD, and CERTICAN® (Novartis), is a novel macrolide immunosuppressant that was developed by Novartis (Nashan, B., Transplantation Proceedings (2001) 33: 3215-3230) in an effort to improve upon sirolimus. Everolimus has greater stability and enhanced solubility in organic solvents, as well as more favorable pharmokinetics with fewer side effects, than sirolimus. The structure of everolimus is shown in Formula III below.

Formula III

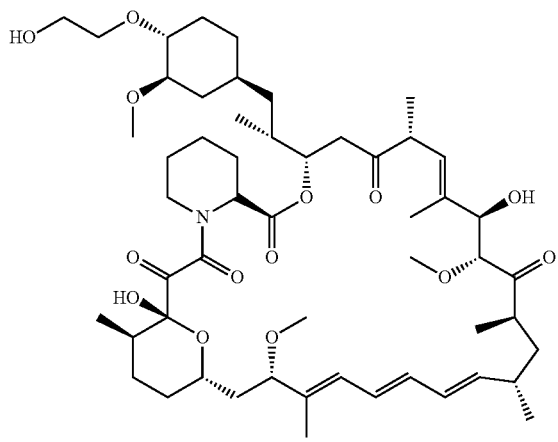

However, there exists a similar need for therapeutic drug monitoring (TDM) with everolimus as with tacrolimus and sirolimus. Immunoassays for everolimus are disclosed, for example, in U.S. Pat. No. 7,223,553.

As stated herein above, the side effects associated with these immunosuppressant drugs can be controlled in part by carefully controlling the level of the drug present in a patient. Therapeutic monitoring of concentrations of immunosuppressant drugs and related drugs in biological samples is required to optimize dosing regimens to ensure maximal immunosuppression with minimal toxicity. Although immunosuppressant drugs are highly effective immunosuppressive agents, their use must be carefully managed, because the effective dose range is often narrow, and excessive dosage can result in serious side effects. On the other hand, too little dosage of an immunosuppressant can lead to tissue rejection. Because distribution and metabolism of an immunosuppressant drug can vary greatly between patients, and because of a wide range and severity of adverse reactions, accurate monitoring of the drug level is essential.

However, therapeutic drug monitoring (TDM) of immunophilin-binding drugs is particularly difficult, given that the binding of immunophilins endogenously present in biological samples will interfere with the assay. One method that has been utilized to attempt to overcome this interference is to add a substance that acts as a "displacer" by displacing the drug from its endogenous binding protein(s). In particular, tacrolimus, sirolimus, and everolimus are very closely related, and the use of one of these drugs to displace another drug from its endogenous binding proteins has been attempted. For example, U.S. Pat. No. 6,187,547 discloses the use of these immunosuppressive drugs (ISD) with similar chemical structure to displace another ISD (i.e., the use of sirolimus to displace tacrolimus and vice versa). However, this approach is not adaptable to random access automated immunoassay systems because of the potential for reagent carry-over; that is, the use of sirolimus to displace tacrolimus in a tacrolimus immunoassay may contaminate other assays, such as (but not limited to) the sirolimus immunoassay.

U.S. Pat. No. 7,186,518 discloses the use of a number of FK506 (tacrolimus) derivatives to displace FK506 from its endogenous binding proteins. However, these compounds showed varying degrees of cross-reactivity to the parent drug and to new antibodies that had been developed for the assay. For example, the FK ester disclosed in the '518 patent is recognized by the 1E2 antibody clone that is used in the new tacrolimus assay (U.S. Pat. No. 8,586,322). For that reason, the new tacrolimus assay utilizing the 1E2 antibody clone must use sirolimus as the displacer; however, as stated above, the use of sirolimus as the displacer runs the risk of reagent carry-over and contamination of other assays (such as the sirolimus assay).

Therefore, there is a need in the art for new and improved binding competitors for use in assays for macrophilin-binding pharmaceuticals within a biological sample that overcome the disadvantages and defects of the prior art. It is to such compositions, as well as kits containing same and methods of using same, that the present disclosure is directed.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1 graphically depicts standard curves of an everolimus assay performed in the absence and presence of various displacers known in the art and constructed in accordance with the present disclosure.

DETAILED DESCRIPTION

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions, kits, and/or methods disclosed herein can be made and executed without undue experimentation in light of the present disclosure. While the compositions, kits, and/or methods have been described in terms of particular embodiments, it will be apparent to those of skill in the art that variations may be applied to the compositions, kits, and/or methods and in the steps or in the sequence of steps of the methods described herein without departing from the concept, spirit, and scope of the present disclosure. All such similar substitutes and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The terms "analog" and "derivative" are used herein interchangeably and refer to a substance which comprises the same basic carbon skeleton and carbon functionality in its structure as a given compound, but can also contain one or more substitutions thereto. The term "substitution" as used herein will be understood to refer to the replacement of at least one substituent on a compound with a residue R. In certain non-limiting embodiments, R may include H, hydroxyl, thiol, a halogenid selected from fluoride, chloride bromide or iodite, a C1-C4 compound selected one of the following: linear, branched or cyclic alkyl, optionally substituted, and linear branched or cyclic alkenyl, wherein the optional substitutents are selected from one or more alkenylalkyl, alkynylalkyl, cycloalkyl, cycloalkenylalkyl, arylalkyl, heteroarylalkyl, heterocyclealkyl, optionally substituted heterocycloalkenylalkyl, arylcycloalkyl, and arylheterocycloalkyl, each of which is optionally substituted wherein the optional substitutents are selected from one or more of alkenylalkyl, alkynylalkyl, cycloalkyl, cyclalkenylalkyl, arylalkyl, alkylaryl, heteroarylalkyl, heterocyclealkyl, optionally substituted heterocycloalkenylalkyl, arylcycloalkyl, and arylheterocyclalkyl, phenyl, cyano, hydroxyl, alkyl, aryl, cycloalkyl, cyano, alkoxy, alkylthio, amino, —NH (alkyl), —NH(cycloalkyl)$_2$, carboxy, and —C(O))-alkyl.

The term "sample" as used herein will be understood to include any type of biological sample that may be utilized in accordance with the present disclosure. Examples of fluidic biological samples that may be utilized include, but are not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, combinations thereof, and the like.

The term "specific binding partner," as used herein, will be understood to refer to any molecule capable of specifically associating with a macrophilin-binding pharmaceutical for purposes of detection thereof. For example, but not by way of limitation, the specific binding partner may be an antibody, a receptor, a ligand, an aptamer, a molecular imprinted polymer (i.e., inorganic matrices), or any combination and/or derivative(s) thereof, as well as any other molecules capable of specific binding to the macrophilin-binding pharmaceutical.

The term "antibody" is used herein in the broadest sense and refers to, for example, intact monoclonal antibodies and polyclonal antibodies, multi-specific antibodies (e.g., bispecific antibodies), antibody fragments and conjugates thereof that exhibit the desired biological activity of analyte binding (such as, but not limited to, Fab, Fab', F(ab')2, Fv, scFv, Fd, diabodies, single-chain antibodies, and other antibody fragments and conjugates thereof that retain at least a portion of the variable region of an intact antibody), antibody substitute proteins or peptides (i.e., engineered binding proteins/peptides), and combinations or derivatives thereof. The antibody can be of any type or class (e.g., IgG, IgE, IgM, IgD, and IgA) or sub-class (e.g., IgG1, IgG2, IgG3, IgG4, IgA1, and IgA2).

Certain non-limiting embodiments of the present disclosure are directed to compositions that include at least one of the compounds represented in Formulas IV, V, VI, and VII below:

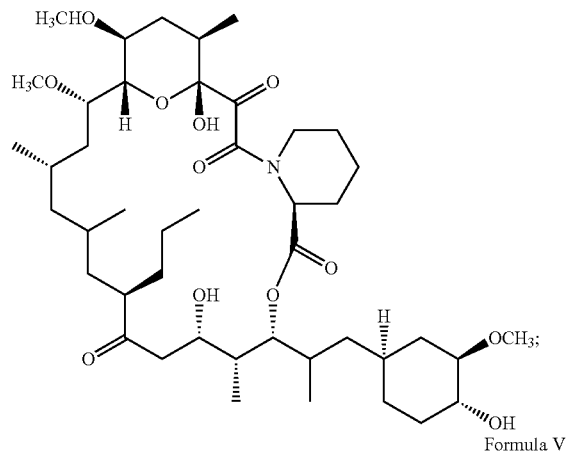

Formula IV

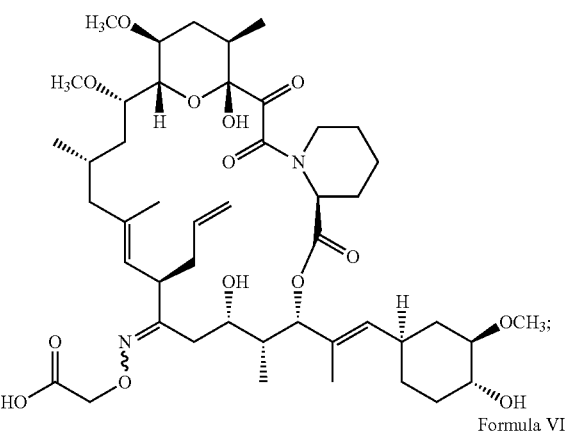

Formula V

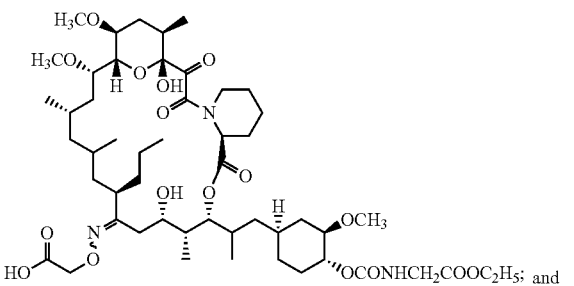

Formula VI

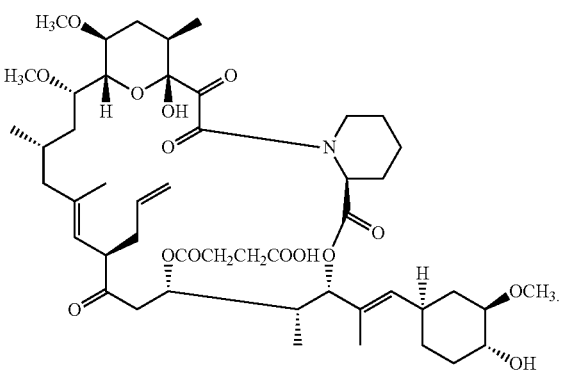

Formula VII

In a particular (but non-limiting) embodiment, the composition includes at least the compound represented by Formula IV.

In a particular (but non-limiting) embodiment, the composition includes at least the compound represented by Formula V.

In a particular (but non-limiting) embodiment, the composition includes at least the compound represented by Formula VI.

In a particular (but non-limiting) embodiment, the composition includes at least the compound represented by Formula VII.

In particular (but non-limiting) embodiments, each of the above compounds is defined as a binding competitor for use in an assay for a macrophilin-binding pharmaceutical. For example, but not by way of limitation, the macrophilin-binding pharmaceutical may be at least one of everolimus, sirolimus (rapamycin), and tacrolimus (FK506). In certain non-limiting embodiments, the compound does not substantially cross-react with a specific binding partner for the macrophilin-binding pharmaceutical utilized in the assay.

Certain non-limiting embodiments of the present disclosure are also directed to a method of determining the presence of a macrophilin-binding pharmaceutical in a sample. In the method, any of the binding competitors disclosed or otherwise contemplated herein is added to a sample to displace the macrophilin-binding pharmaceutical from its immunophilin complexes. A macrophilin-binding pharmaceutical-specific binding partner that binds to the pharmaceutical but does not significantly bind to the binding competitor is then added to form a binding partner/pharmaceutical complex. The binding partner/pharmaceutical complex is then detected, and the detection is correlated with an amount of pharmaceutical present in the sample.

Any sample for which an assay for the presence of a macrophilin-binding pharmaceutical is desired can be utilized as the sample in accordance with the methods of the present disclosure. Non-limiting examples of samples include a biological sample such as, but not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof.

In certain non-limiting embodiments, the binding competitor is defined as being represented by at least one of Formulas IV-VII. In a particular (but non-limiting) embodiment, the binding competitor is the compound represented by Formula IV. In a particular (but non-limiting) embodiment, the binding competitor is the compound represented by Formula V. In a particular (but non-limiting) embodiment, the binding competitor is the compound represented by Formula VI. In a particular (but non-limiting) embodiment, the binding competitor is the compound represented by Formula VII.

In particular (but non-limiting) embodiments, the macrophilin-binding pharmaceutical is at least one of everolimus, sirolimus (rapamycin), and tacrolimus (FK506). In a particular (but non-limiting) embodiment, the macrophilin-binding pharmaceutical is everolimus. In a particular (but non-limiting) embodiment, the macrophilin-binding pharmaceutical is sirolimus (rapamycin). In a particular (but non-limiting) embodiment, the macrophilin-binding pharmaceutical is tacrolimus (FK506).

Any type of macrophilin-binding pharmaceutical specific binding partners known in the art or otherwise contemplated herein may be utilized in accordance with the present disclosure. In particular (but non-limiting) embodiments, the specific binding partner utilized in the assay is an antibody specific for the macrophilin-binding pharmaceutical. Non-limiting examples of antibodies that may be utilized in accordance with the methods are known in the art and include antibodies against tacrolimus, as disclosed in U.S. Pat. No. 8,586,322; antibodies against rapamycin (sirolimus), as disclosed in U.S. Pat. Nos. 6,635,745; 8,039,599; and 8,039,600; as well as US Patent Application Publication No. 2017/0362305; and antibodies against everolimus, as disclosed in U.S. Pat. No. 7,223,553 and US Patent Application Publication No. 2005/0208607.

In a particular (but non-limiting) example, the antibody utilized in the assay is a monoclonal antibody against tacrolimus, such as (but not limited to), the 14H04 or 1E2 monoclonal antibody clones disclosed previously in U.S. Pat. No. 8,586,322, or the 1H06 clone raised against the same immunogen as 14H04. The '322 patent provides the following definitions for these two antibody clones: (a) a monoclonal antibody that specifically binds to a portion of tacrolimus consisting essentially of the C29-C34 ring including the methoxy and hydroxyl substituents and C15 including the methoxy substituent (clone 14H04); (b) a monoclonal antibody that specifically binds to a portion of tacrolimus consisting essentially of the methoxy of the C10-C14 ring and C19-C27 of the C1-C26 ring including the C22 keto oxygen (clone 1E2); (c) a monoclonal antibody raised against an immunogen comprising an immunogenic carrier linked to tacrolimus at C22 (clones 14H04 and 1H06); (d) a monoclonal antibody raised against an immunogen comprising an immunogenic carrier linked to tacrolimus at C24 (clone 1E2); (e) a monoclonal antibody raised against an immunogen comprising an immunogenic carrier linked to tacrolimus at C32 (clone 1E2); and (f) a monoclonal antibody raised against an immunogen comprising an immunogenic carrier linked to tacrolimus at C24 and C32 (clone 1E2).

The 1H06 clone was raised against an immunogen containing FK coupled via oxime in 22 position and requires a C-22 coupled analog. This monoclonal antibody possesses a good cross-reactivity pattern and has an established affinity in the LOCI assay of KD<$3*10^{-9}$.

In another particular (but non-limiting) embodiment, the antibody utilized in the assay is a monoclonal antibody against sirolimus. Non-limiting examples thereof include the IgG2aK clone, for which the immunogen is at the position C-32; and clones 3H9 (IgG1λ) and 165 (IgG2aK), which were raised against an immunogen comprising a C26 & C32 mixture. Thus, additional non-limiting examples of monoclonal antibodies that can be utilized in accordance with the present disclosure include (g) a monoclonal antibody raised against an immunogen comprising an immunogenic carrier linked to sirolimus at C32; and (h) a monoclonal antibody raised against a mixture of an immunogen comprising an immunogenic carrier linked to sirolimus at C26 and an immunogen comprising an immunogenic carrier linked to sirolimus at C32.

Certain non-limiting embodiments of the present disclosure are also directed to a kit for the detection of the presence of a macrophilin-binding pharmaceutical in a sample. The kit comprises one or more of any of the binding competitors that displaces a macrophilin-binding pharmaceutical from its immunophilin complexes as disclosed or otherwise contemplated herein.

In certain non-limiting embodiments, the binding competitor is defined as being represented by at least one of Formulas IV-VII. In a particular (but non-limiting) embodiment, the binding competitor is the compound represented by Formula IV. In a particular (but non-limiting) embodiment, the binding competitor is the compound represented by Formula V. In a particular (but non-limiting) embodiment, the binding competitor is the compound represented by Formula VI. In a particular (but non-limiting) embodiment, the binding competitor is the compound represented by Formula VII.

In particular (but non-limiting) embodiments, the macrophilin-binding pharmaceutical is at least one of everolimus, sirolimus (rapamycin), and tacrolimus (FK506). In a particular (but non-limiting) embodiment, the macrophilin-binding pharmaceutical is everolimus. In a particular (but non-limiting) embodiment, the macrophilin-binding pharmaceutical is sirolimus (rapamycin). In a particular (but non-limiting) embodiment, the macrophilin-binding pharmaceutical is tacrolimus (FK506).

In a particular (but non-limiting) embodiment, the kit may further comprise one or more of any of the macrophilin-binding pharmaceutical-specific binding partners that binds to the pharmaceutical for detection of a binding partner/pharmaceutical complex (wherein the binding partner does not significantly bind to the binding competitor), as described or otherwise contemplated herein.

Any type of macrophilin-binding pharmaceutical specific binding partners known in the art or otherwise contemplated herein may be utilized in accordance with the present disclosure. In particular (but non-limiting) embodiments, the specific binding partner utilized in the assay is an antibody specific for the macrophilin-binding pharmaceutical. Non-limiting examples of antibodies that may be utilized in accordance with the methods are known in the art and include antibodies against tacrolimus, as disclosed in U.S. Pat. No. 8,586,322; antibodies against rapamycin (sirolimus), as disclosed in U.S. Pat. Nos. 6,635,745; 8,039,599; and 8,039,600; as well as US Patent Application Publication No. 2017/0362305; and antibodies against everolimus, as disclosed in U.S. Pat. No. 7,223,553 and US Patent Application Publication No. 2005/0208607.

In a particular (but non-limiting) example, the antibody utilized in the assay is a monoclonal antibody against tacrolimus, such as (but not limited to), the 14H04 or 1E2 monoclonal antibody clones disclosed previously in U.S. Pat. No. 8,586,322, or the 1H06 clone raised against the same immunogen as 14H04. Particular non-limiting examples of antibodies that can be utilized in accordance with the present disclosure include: (a) a monoclonal antibody that specifically binds to a portion of tacrolimus consisting essentially of the C29-C34 ring including the methoxy and hydroxyl substituents and C15 including the methoxy substituent; (b) a monoclonal antibody that specifically binds to a portion of tacrolimus consisting essentially of the methoxy of the C10-C14 ring and C19-C27 of the C1-C26 ring including the C22 keto oxygen; (c) a monoclonal antibody raised against an immunogen comprising an immunogenic carrier linked to tacrolimus at C22; (d) a monoclonal antibody raised against an immunogen comprising an immunogenic carrier linked to tacrolimus at C24; (e) a monoclonal antibody raised against an immunogen comprising an immunogenic carrier linked to tacrolimus at C32; (f) a monoclonal antibody raised against an immunogen comprising an immunogenic carrier linked to tacrolimus at C24 and C32; (g) a monoclonal antibody raised against an immunogen comprising an immunogenic carrier linked to sirolimus at C32; and (h) a monoclonal antibody raised against a mixture of an immunogen comprising an immunogenic carrier linked to sirolimus at C26 and an immunogen comprising an immunogenic carrier linked to sirolimus at C32.

The assay components/reagents of the compositions/kits/methods may be provided in any form that allows them to function in accordance with the present disclosure. For example, but not by way of limitation, each of the reagents may be provided in liquid form and disposed in bulk and/or single aliquot form within the kit. Alternatively, in a particular (but non-limiting) embodiment, one or more of the reagents may be disposed in the kit in the form of a single aliquot lyophilized reagent. The use of dried reagents in microfluidics devices is described in detail in U.S. Pat. No. 9,244,085 (Samproni), the entire contents of which are hereby expressly incorporated herein by reference.

In addition to the assay components/reagents described in detail herein above, the kits may further contain other reagent(s) for conducting any of the particular assays described or otherwise contemplated herein. The nature of these additional reagent(s) will depend upon the particular assay format, and identification thereof is well within the skill of one of ordinary skill in the art; therefore, no further description thereof is deemed necessary. Also, the components/reagents present in the kits may each be in separate containers/compartments, or various components/reagents can be combined in one or more containers/compartments, depending on the cross-reactivity and stability of the components/reagents. In addition, the kit may include a microfluidics device in which the components/reagents are disposed.

The relative amounts of the various components/reagents in the kits can vary widely to provide for concentrations of the components/reagents that substantially optimize the reactions that need to occur during the assay methods and further to optimize substantially the sensitivity of an assay. Under appropriate circumstances, one or more of the components/reagents in the kit can be provided as a dry powder, such as a lyophilized powder, and the kit may further include excipient(s) for dissolution of the dried reagents; in this manner, a reagent solution having the appropriate concentrations for performing a method or assay in accordance with the present disclosure can be obtained from these components. Positive and/or negative controls may also be included with the kit. In addition, the kit can further include a set of written instructions explaining how to use the kit. A kit of this nature can be used in any of the methods described or otherwise contemplated herein.

EXAMPLES

Examples are provided hereinbelow. However, the present disclosure is to be understood to not be limited in its application to the specific experimentation, results, and laboratory procedures disclosed herein. Rather, the Examples are simply provided as one of various embodiments and are meant to be exemplary, not exhaustive.

Example 1

In this Example, an everolimus assay was conducted in the absence and presence of various displacers, as described in detail herein below.

The automated DIMENSION® assay system (Siemens Healthcare Diagnostics Inc., Tarrytown, NY), the everolimus (EVRO) assay method uses an immunoassay technique in which free and everolimus-bound antibody-enzyme conjugate is separated using magnetic particles. The assay antibody used for this assay is a mouse monoclonal antibody (cell line: 155-M1). The assay was performed using a method specific FLEX® reagent cartridge (Siemens Healthcare Diagnostics Inc., Tarrytown, NY). The FLEX® reagent cartridge contains a pretreatment reagent, antibody-β-galactosidase conjugate, everolimus analog immobilized on chromium dioxide particles, chlorophenol red β-d-galactopyranoside (CPRG) substrate, and diluent to hydrate the tablets. To perform the EVRO assay, a sample cup (or SSC) containing the whole blood sample to be analyzed and an EVRO FLEX® reagent cartridge were placed appropriately on the DIMENSION® system. The DIMENSION® system mixed and lysed the whole blood sample in the presence of the pretreatment reagent that contains detergents and a displacer (FK506 or FK506 analogs as described previously). This reagent contains a displacer which acts to displace everolimus in the sample from endogenous binding proteins (immunophilins such as FKBPs, etc.). The lysed sample was then mixed with the antibody enzyme conjugate. The everolimus present in the sample was bound by the everolimus antibody. Magnetic particles coated with everolimus analog were added to bind free (unbound) antibody-enzyme conjugate. The reaction mixture was then separated magnetically. Following separation, the supernatant containing the everolimus-antibody-enzyme complex was transferred to a cuvette and mixed with the substrate, chlorophenol red β-d-galactopyranoside (CPRG). β-galactosidase catalyzes the hydrolysis of CPRG to produce chlorophenol red (CPR) that absorbs light maximally at 577 nm. The change in absorbance at 577 nm due to the formation of CPR is directly proportional to the amount of everolimus in the patient's sample and is measured using a bichromatic (577 nm, 700 nm) rate technique.

The assay was conducted in the absence of any displacer as well as in the presence of the following displacers: tacrolimus (FK506, as represented by Formula I), FK506 Ester (disclosed in U.S. Pat. No. 7,186,518), FK506 C24 succinate (as represented by Formula VII), Reduced FK506 (as represented by Formula IV), FK506 22-oxime-32-isocyanatoacetatethyl ester (as represented by Formula VI), and FK506 oxime (as represented by Formula V). Standard curves for the everolimus assay with and without displacer were constructed, as shown in FIG. 1 and Table 1.

tivities detected for the various displacers of the present disclosure with the tacrolimus assay antibody (1E2 clone).

As shown in Table 2, the cross-reactivity of each of the tacrolimus analogs with the antibody used in the everolimus assay is tested to ensure that there is substantially no cross-reactivity between the antibody against everolimus and not only the parent drug (tacrolimus, FK506) but also each of the analogs thereof being utilized as displacers in the everolimus assay. It is imperative to ensure that the structural alterations made to the parent drug do not render the analogs "close enough" to everolimus to cross-react with the everolimus assay antibody. As can be seen in Table 2, there is substantially no cross-reactivity between the everolimus assay antibody and tacrolimus (FK506), and there is also substantially no cross-reactivity between the everolimus assay antibody and each of the FK506 analogs tested.

TABLE 2

| CROSS-REACTIVITY WITH EVEROLIMUS ASSAY ANTIBODY (155-M1 Clone) | | |
| --- | --- | --- |
| Analog | Formula of Analog | % Cross-Reactivity |
| FK506 | I | 0.01% |
| FK506 Ester | (from '518 patent) | 0.00% |
| 24-Succinate FK506 | VII | 0.01% |
| FK-0001 | IV | 0.02% |
| FK-506-1 | VI | 0.02% |
| FK506 Oxime | V | 0.02% |

Next, the cross-reactivity of each of the analogs used in the everolimus assay was tested with the antibody used in the tacrolimus assay (Table 3). While efforts may be made to minimize reagent carryover from the everolimus assay to the tacrolimus assay, an automated instrument may run both everolimus and tacrolimus (or sirolimus) assays simultaneously. Therefore, due to the use of a large amount of displacer (tacrolimus analogs) present in the everolimus assay, the displacer could be carried into the tacrolimus assay, and this would cause a falsely elevated signal in the tacrolimus assay if cross-reaction were observed. So if a

TABLE 1

| EVEROLIMUS STANDARD CURVES WITH AND WITHOUT DISPLACERS | | | | | | | |
| --- | --- | --- | --- | --- | --- | --- | --- |
| BV (ng/mL) | No displacer | Tacrolimus (FK506) | FK506 Ester | FK506 C24 Succinate | Reduced FK506 | FK506 22-oxime-32-iso-cyanatoacetatethyl ester | FK506 Oxime |
| 0 | 16 | 17 | 16 | 16 | 17 | 18 | 17 |
| 5.5 | 33 | 67 | 62 | 71 | 61 | 68 | 60 |
| 11.2 | 48 | 104 | 97 | 108 | 94 | 102 | 90 |
| 21.9 | 76 | 143 | 135 | 145 | 132 | 140 | 131 |
| 34.3 | 100 | 156 | 151 | 157 | 149 | 154 | 149 |

As can be seen from FIG. 1 and Table 1, each of the displacers functioned as a binding competitor to displace the assayed drug (everolimus) from its endogenous binding proteins. In this manner, the freed drug molecules that were previously blocked by the binding proteins are now accessible by the assay antibody, thereby increasing the amount of everolimus signal detected in the assay.

Now that the displacers of the present disclosure were shown to be effective as binding competitors, the displacers were also tested for any cross reactivity with antibodies utilized in the ISD assays of the present disclosure. Table 2 indicates the cross-reactivities detected for the various displacers of the present disclosure with the everolimus assay antibody (155-M1), while Table 3 indicates the cross-reactacrolimus analog (e.g. 24-succinate FK506) shows a lower cross-reactivity with the tacrolimus assay antibody, using the tacrolimus analog as the displacer in the everolimus assay can lower the risk of reagent carry-over and falsely elevated signal in the tacrolimus assay.

As can be seen in Table 3, the analog disclosed in the '518 patent has a sufficient level of cross-reactivity with the tacrolimus assay antibody to prevent its use in an automated system where a tacrolimus assay is also performed (whether simultaneously or sequentially with the everolimus assay). In contrast, the analogs of Formulas IV, V, VI, and VII all possessed much lower cross-reactivities and thus would be much more amenable to use in an automated assay system that performs both assays.

TABLE 3

CROSS-REACTIVITY WITH TACROLIMUS ASSAY ANTIBODY (1E2 Clone)

| Analog | Formula of Analog | % Cross-Reactivity |
|---|---|---|
| FK506 | I | 100% |
| FK506 Ester | (from '518 patent) | 23.3% |
| 24-Succinate FK506 | VII | 13.3% |
| FK-0001 | IV | 4.6% |
| FK-506-1 | VI | 1.5% |
| FK506 Oxime | V | 4.0% |

The ability of the FK analogs to displace everolimus drug in the everolimus assay is a function of their FKBP (macrophilin) binding. So the curve size after adding the displacer indicates the ability of their FKBP binding: the larger the curve size, the better the binding.

While not wishing to be bound to a specific mechanism or theory, it may be possible to explain why some compounds showed a larger curve size than others based upon the teachings of Van Duyne et al. (*J. Am. Chem. Soc.* (1991) 113(19):7433-7434; and *J. Mol. Biol.* (1993) 229:105-124). An FK506 analog was also produced that was modified at the C32 position, but this FK506 analog showed little binding (or signal enhancement vs. no displacer; results not shown), which is consistent with the atomic structures described in these references. Thus, while not wishing to be bound by any theory, it is noted that it may be possible to relate the curve size to modification sites on the FK506 molecule.

Thus, in accordance with the present disclosure, there have been provided compositions, kits, and devices, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A composition comprising at least one of:
   (a) the compound represented by Formula IV:

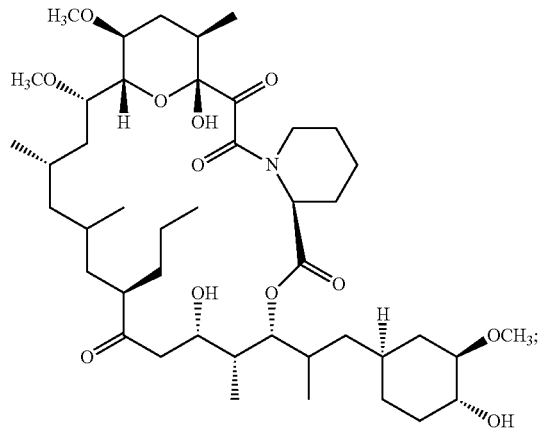 [SMILES: CCC[C@@H]1CC(C)C[C@H](C)C[C@H](OC)[C@H]2O[C@@](O)(C(=O)C(=O)N3CCCC[C@H]3C(=O)O[C@H](C(C)C[C@@H]3CC[C@@H](O)[C@H](OC)C3)[C@H](C)[C@@H](O)CC1=O)[C@H](C)C[C@@H]2OC]

and
   (b) the compound represented by Formula VI:

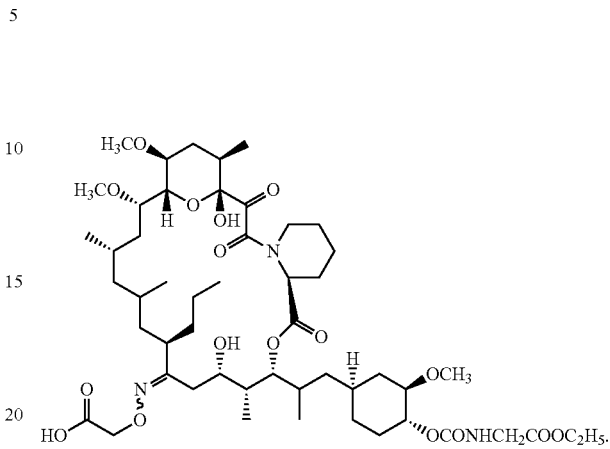

2. The composition of claim 1, wherein the compound is further defined as a binding competitor for use in an assay for a macrophilin-binding pharmaceutical.

3. The composition of claim 2, wherein the macrophilin-binding pharmaceutical is at least one of everolimus, sirolimus, and tacrolimus.

4. The composition of claim 2, wherein the compound does not substantially cross-react with a specific binding partner for the macrophilin-binding pharmaceutical utilized in the assay.

5. A method of determining the presence of a macrophilin-binding pharmaceutical in a sample, the method comprising the steps of:

adding to the sample a binding competitor to displace the macrophilin-binding pharmaceutical from its immunophilin complexes, wherein the binding competitor is at least one of:

(a) the compound represented by Formula IV:

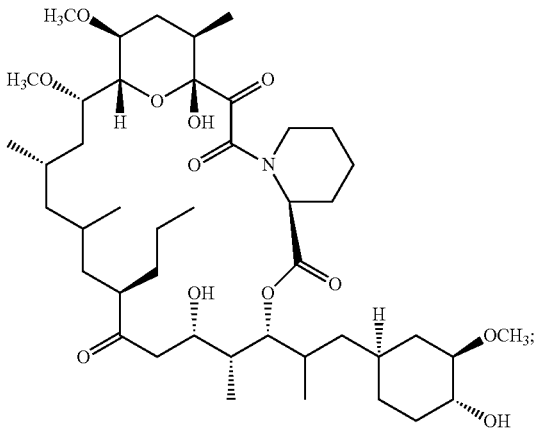 [SMILES: CCC[C@@H]1CC(C)C[C@H](C)C[C@H](OC)[C@H]2O[C@@](O)(C(=O)C(=O)N3CCCC[C@H]3C(=O)O[C@H](C(C)C[C@@H]3CC[C@@H](O)[C@H](OC)C3)[C@H](C)[C@@H](O)CC1=O)[C@H](C)C[C@@H]2OC]

(b) the compound represented by Formula V:

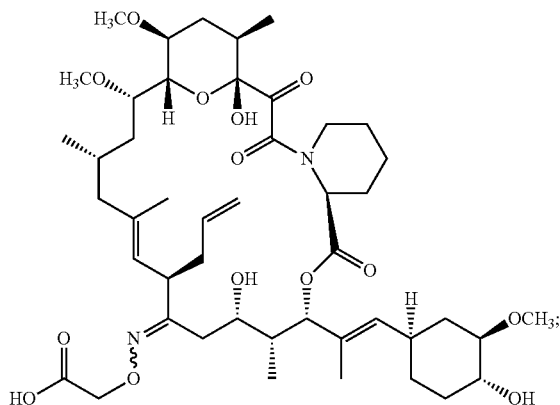 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=NOCC(=O)O)[C@H](C)C[C@@H]2OC]

(c) the compound represented by Formula VI:

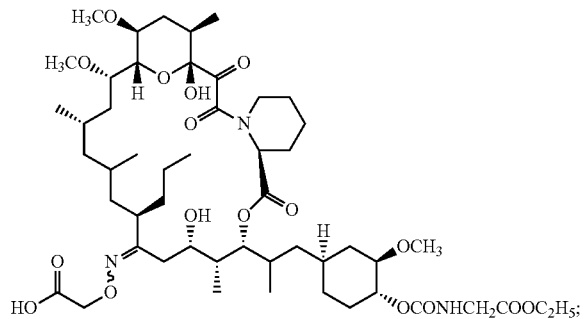

or (d) the compound represented by Formula VII:

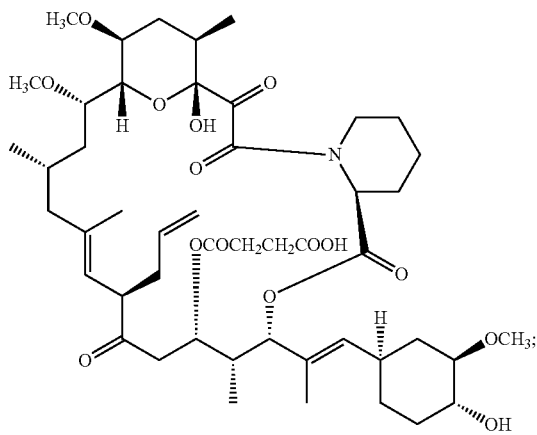

adding a macrophilin-binding pharmaceutical-specific binding partner that binds to the pharmaceutical to form a binding partner/pharmaceutical complex, and wherein the binding partner does not significantly bind to the binding competitor; and detecting the binding partner/pharmaceutical complex and correlating the detection with an amount of pharmaceutical present in the sample.

6. The method of claim 5, wherein the macrophilin-binding pharmaceutical is at least one of everolimus, sirolimus, and tacrolimus.

7. The method of claim 5, wherein the specific binding partner is an antibody specific for the macrophilin-binding pharmaceutical.

8. The method of claim 7, wherein the antibody is at least one of:
(a) a monoclonal antibody that specifically binds to a portion of tacrolimus consisting essentially of the C29-C34 ring including the methoxy and hydroxyl substituents and C15 including the methoxy substituent;
(b) a monoclonal antibody that specifically binds to a portion of tacrolimus consisting essentially of the methoxy of the C10-C14 ring and C19-C27 of the C1-C26 ring including the C22 keto oxygen;
(c) a monoclonal antibody raised against an immunogen comprising an immunogenic carrier linked to tacrolimus at C22;
(d) a monoclonal antibody raised against an immunogen comprising an immunogenic carrier linked to tacrolimus at C24;
(e) a monoclonal antibody raised against an immunogen comprising an immunogenic carrier linked to tacrolimus at C32;
(f) a monoclonal antibody raised against an immunogen comprising an immunogenic carrier linked to tacrolimus at C24 and C32;
(g) a monoclonal antibody raised against an immunogen comprising an immunogenic carrier linked to sirolimus at C32; and
(h) a monoclonal antibody raised against a mixture of an immunogen comprising an immunogenic carrier linked to sirolimus at C26 and an immunogen comprising an immunogenic carrier linked to sirolimus at C32.

9. The method of claim 5, wherein the binding competitor is the compound represented by Formula IV.

10. The method of claim 5, wherein the binding competitor is the compound represented by Formula V.

11. The method of claim 5, wherein the binding competitor is the compound represented by Formula VI.

12. The method of claim 5, wherein the binding competitor is the compound represented by Formula VII.

13. A kit for the detection of the presence of a macrophilin-binding pharmaceutical in a sample, the kit comprising:
a binding competitor that displaces the macrophilin-binding pharmaceutical from its immunophilin complexes, wherein the binding competitor is at least one of:
(a) the compound represented by Formula IV:

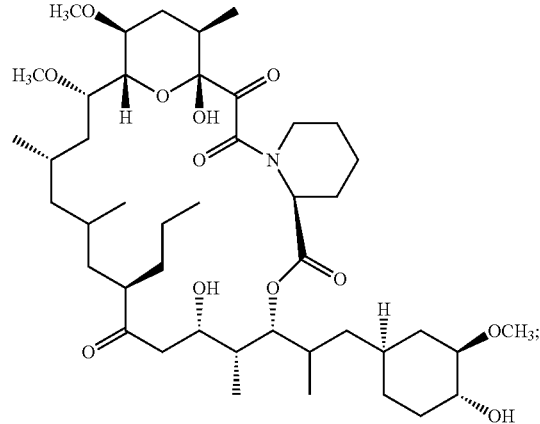 [SMILES: CCC[C@@H]1CC(C)C[C@H](C)C[C@H](OC)[C@H]2O[C@@](O)(C(=O)C(=O)N3CCCC[C@H]3C(=O)O[C@H](C(C)C[C@@H]3CC[C@@H](O)[C@H](OC)C3)[C@H](C)[C@@H](O)CC1=O)[C@H](C)C[C@@H]2OC]

(b) the compound represented by Formula V:

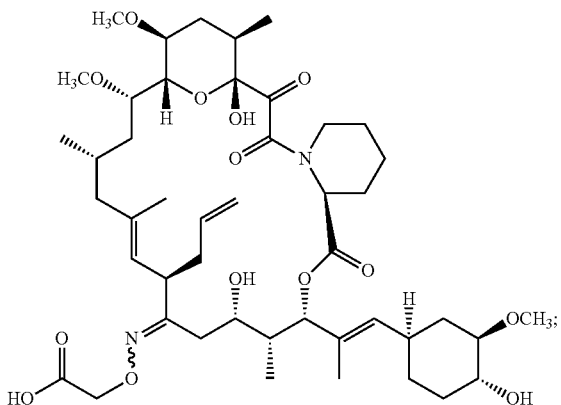 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=NOCC(=O)O)[C@H](C)C[C@@H]2OC]

(c) the compound represented by Formula VI:

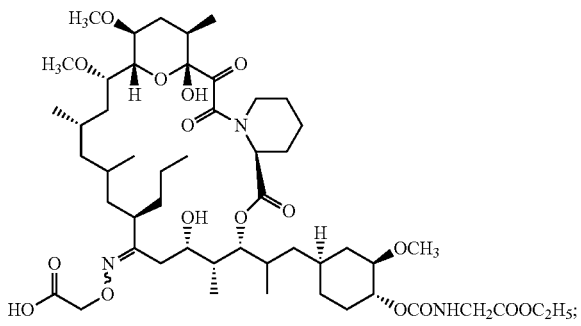

or
(d) the compound represented by Formula VII:

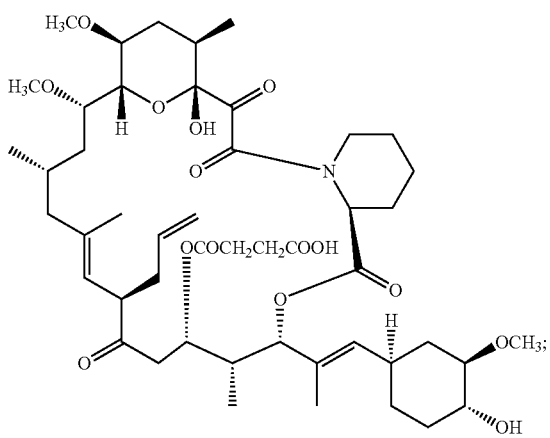

and a macrophilin-binding pharmaceutical-specific binding partner that binds to the pharmaceutical for detection of a binding partner/pharmaceutical complex, and wherein the binding partner does not significantly bind to the binding competitor.

14. The kit of claim 13, wherein the macrophilin-binding pharmaceutical is at least one of everolimus, sirolimus, and tacrolimus.

15. The kit of claim 13, wherein the specific binding partner is an antibody specific for the macrophilin-binding pharmaceutical.

16. The kit of claim 15, wherein the antibody is at least one of:

(a) a monoclonal antibody that specifically binds to a portion of tacrolimus consisting essentially of the C29-C34 ring including the methoxy and hydroxyl substituents and C15 including the methoxy substituent;

(b) a monoclonal antibody that specifically binds to a portion of tacrolimus consisting essentially of the methoxy of the C10-C14 ring and C19-C27 of the C1-C26 ring including the C22 keto oxygen;

(c) a monoclonal antibody raised against an immunogen comprising an immunogenic carrier linked to tacrolimus at C22;

(d) a monoclonal antibody raised against an immunogen comprising an immunogenic carrier linked to tacrolimus at C24;

(e) a monoclonal antibody raised against an immunogen comprising an immunogenic carrier linked to tacrolimus at C32;

(f) a monoclonal antibody raised against an immunogen comprising an immunogenic carrier linked to tacrolimus at C24 and C32;

(g) a monoclonal antibody raised against an immunogen comprising an immunogenic carrier linked to sirolimus at C32; and (h) a monoclonal antibody raised against a mixture of an immunogen comprising an immunogenic carrier linked to sirolimus at C26 and an immunogen comprising an immunogenic carrier linked to sirolimus at C32.

17. The kit of claim 13, wherein the binding competitor is the compound represented by Formula IV.

18. The kit of claim 13, wherein the binding competitor is the compound represented by Formula V.

19. The kit of claim 13, wherein the binding competitor is the compound represented by Formula VI.

20. The kit of claim 13, wherein the binding competitor is the compound represented by Formula VII.

* * * * *